US00RE44035E

(19) United States
(12) Reissued Patent
Schamber et al.

(10) Patent Number: US RE44,035 E
(45) Date of Reissued Patent: Mar. 5, 2013

(54) APPARATUS FOR CORRELATING AN OPTICAL IMAGE AND A SEM IMAGE AND METHOD OF USE THEREOF

(75) Inventors: Frederick H. Schamber, Murrysville, PA (US); Cornelis G. van Beek, Pittsburgh, PA (US); Nicholas Ritchie, Laytonsville, MD (US)

(73) Assignee: FEI Company, Hillsboro, OR (US)

(21) Appl. No.: 12/360,920

(22) Filed: Jan. 28, 2009

Related U.S. Patent Documents

Reissue of:
(64) Patent No.: 6,683,316
Issued: Jan. 27, 2004
Appl. No.: 10/210,242
Filed: Aug. 1, 2002

U.S. Applications:
(60) Provisional application No. 60/309,367, filed on Aug. 1, 2001.

(51) Int. Cl.
*H01J 37/26* (2006.01)
*H01J 37/36* (2006.01)

(52) U.S. Cl. ..... 250/492.1; 250/492.2; 250/311; 250/310

(58) Field of Classification Search ..... 250/492.1, 250/310, 311, 492.21, 397, 307
See application file for complete search history.

(56) References Cited

U.S. PATENT DOCUMENTS

| | | | | |
|---|---|---|---|---|
| 4,843,246 | A * | 6/1989 | Benes et al. | 250/491.1 |
| 5,905,266 | A * | 5/1999 | Larduinat et al. | 250/494.21 |
| 6,031,985 | A * | 2/2000 | Yoshida | 714/738 |
| 6,172,363 | B1 * | 1/2001 | Shinada et al. | 850/9 |
| 6,198,299 | B1 * | 3/2001 | Hollman | 324/758 |
| 6,473,228 | B1 * | 10/2002 | Toshimitsu | 359/368 |
| 6,489,625 | B1 * | 12/2002 | Takahashi | 250/559.29 |

OTHER PUBLICATIONS

Schamber, F., "MicroNavigator Navigation software for digital microscopy," Aspex, LLC, 40 pages, 2003.

* cited by examiner

*Primary Examiner* — Jack Berman
*Assistant Examiner* — Johnnie L Smith
(74) *Attorney, Agent, or Firm* — Scheinberg & Associates, PC; Michael O. Scheinberg

(57) ABSTRACT

An instrument system is controlled to acquire an optical image of an object, with the optical image defining a first coordinate system. The object is positioned in a second coordinate system and a point in the optical image is selected. The object is repositioned so that a point on the object corresponding to the selected point in the optical image is positioned at a predetermined point in the second coordinate system. Alternatively, movement of the object causes an indicia on the optical image to move to a point thereon corresponding to the point on the object that is positioned at the predetermined point in the second coordinate system.

30 Claims, 10 Drawing Sheets

APPARATUS FOR CORRELATING AN OPTICAL IMAGE AND A SEM IMAGE AND METHOD OF USE THEREOF

Matter enclosed in heavy brackets [ ] appears in the original patent but forms no part of this reissue specification; matter printed in italics indicates the additions made by reissue.

CROSS REFERENCE TO RELATED APPLICATIONS

This application claims the benefit of U.S. Provisional Patent Application Serial No. 60/309,367, filed Aug. 1, 2001, entitled "Apparatus For Correlating An Optical Image And An SEM Image And Method Of Use Thereof".

BACKGROUND OF THE INVENTION

1. Field of the Invention

The present invention relates to correlating optical and virtual images in electron microscopy.

2. Description of Related Art

A Scanning Electron Microscope (SEM) operates by rastering (scanning) a sharply focused beam of electrons over the surface of a specimen and then displaying on a separate display device a virtual image corresponding to the changing pattern of response signals emanating from the specimen in response to interaction between the electron beam and the specimen. Thus, a point on the specimen which produces a weak response signal appears as a corresponding dark point on the display device, and a point on the specimen which produces an intense response is recorded as a correspondingly bright point on the display. A magnified image is achieved by scanning the electron beam over a small region of the sample and then displaying the response as a virtual image on a much larger display surface. By using a very small electron probe and scanning over very tiny areas, it is possible to achieve magnifications of tens of thousands of times and resolve features in the submicron and even nanometer scale ranges. However, on the other end of the SEM magnification range, because of various practical considerations, a SEM cannot generally scan its beam over an area greater than approximately 1 cm square. In order to inspect larger specimens, it is necessary to manipulate a mechanical positioning stage to bring the desired region of the specimen into view and in this context the narrow field of view of the SEM image presents a practical difficulty for the operator. Because SEM images are, by necessity, created within a vacuum chamber, direct observation of the specimen is not generally possible. Thus, the only visual feedback available to the operator is the SEM image itself. Since the operator can only "see" a small portion of the specimen at one time, it is thus difficult to "navigate" to a particular feature of interest or to move efficiently from one feature to another.

The term "navigation" is used advisedly in this context. Because of the relatively small field of view compared to the relatively large extent of the stage motion or the dimensions of the specimen(s), the SEM operator (particularly the novice) often feels very much like a mariner attempting to locate a landfall without charts or points of reference. Under these circumstances, it is not uncommon for the SEM operator to become confused and even move away from the desired feature. In some cases, operators have been known to damage specimens, staging mechanisms, or detectors due to inappropriate stage manipulation engendered by such confusion.

SEM specimens fall into two general categories: (1) single objects; and (2) collections of objects. As examples of the first category, a forensic specialist might wish to inspect a knife blade or an automotive engineer might wish to inspect a drive gear. In such cases, the portion of the object which can instantaneously be viewed in the SEM represents a fraction of its entirety and it can be quite difficult to locate a particular feature of interest. As an example of the second category, it is common to mount multiple small samples on a common "specimen carrier". For instance, a very common mounting medium used for SEM is the "thumbtack" stub mount—a polished disk of typically one-half inch diameter with a peg protruding from the opposite side. In practice, small specimens (e.g., powders) are fixed to the polished surface and the stub is then mounted to a larger carrier plate which grips the mounting peg. In this manner, multiple stub-mounted samples are attached to a larger carrier which is then mounted on the SEM's positioning stage. The dimension of each stub is roughly comparable to the size of the SEM's maximum field of view, so it is relatively straightforward to navigate within its area, but it can be quite challenging to locate a particular stub on a carrier, particularly when the mounted specimens look similar. So in either case—the situation of single large objects or multiple smaller objects—the small field of view of the SEM creates a complication for efficiently locating a particular feature or object of interest.

Historically, the size of SEM samples and sample chambers has been steadily increasing. Many of the earliest SEMs could handle only one of the one-half inch diameter stubs described above. A modern SEM may be capable of handling very large specimens or very large arrays of specimens—objects of up to 13 inches in diameter or arrays of over one hundred individual specimens can be evaluated in some commercial units. Thus, the problem of efficient navigation has become increasingly important.

Since SEM images are produced by fundamentally different contrast mechanisms than are available in light microscopes, there are many practical situations where it is difficult to correlate a SEM image with an optical image of the same area. The lack of color information in a SEM image is a particularly important issue. Thus, visual "landmarks" may be lacking or obscured in a SEM image, further complicating the navigation problem.

Experienced SEM operators develop skills and techniques to confidently locate specimens and features even under the above-described circumstances, but such skills and techniques are, of course, not possessed by the novice or infrequent user. The SEM has increasingly moved from a role as a purely laboratory instrument into a role as an industrial tool. One consequence is that the individuals who are operating a SEM are less likely to be highly experienced "microscopists" and more likely to be technicians or engineers who are not highly experienced in operating the SEM. These latter individuals are less tolerant of learning specialized skills and more likely to commit errors of operation. Thus, the problem of locating features in a SEM is a practical problem of considerable consequence for the SEM manufacturer.

SEM manufacturers have long been aware of the above "navigation" issue and have devised various expedients to aid the user. The most basic of these expedients is the use of calibrated scales on the knobs used to manipulate the stage positioning controls. By becoming familiar with these scales, experienced microscopists are able to confidently manipulate the specimen to desired coordinates. As motorized stages have become more common and the use of computers to control them more prevalent, the basic mechanical scale concept has evolved correspondingly. Today, instead of turning knobs which directly move the stage, the operator may move the stage by means of a virtual or electronic "joystick" or similar device which communicates with motors which actually cause the stage to be translated. In such case, numerical readouts are commonly provided on the computer screen to indicate the position of the stage. Conceptually, however, this expedient is little more than a refinement of the position scale offered on the earliest SEM stages.

An important step up in sophistication is the provision of a graphical navigation "map". This is simply a graphical representation of the area traversed by the stage and permits the operator to immediately visualize the position of the stage by means of a crosshair or other marker superimposed on the map. Such a "map" may, for example, appear as a "grid" whose equally spaced lines serve to provide relative indications of position. The operator is generally given the option of moving to a given point on the specimen by simply "clicking" a pointing device (such as a computer mouse) at the desired coordinates on the map. A further refinement is to provide a crude graphical representation of the specimen itself on the map (such as circles indicating the boundaries of standard sample stub positions). All of these refinements have been implemented in various forms and are much appreciated by SEM users. However, these are still relatively "abstract" aids and do not directly correspond to the operator's knowledge of the detailed visual morphology of the specimen. For example, a casual user is more likely to remember that the specimen of interest is a reddish-brown rectangle than that it is mounted on the second stub from the upper-right corner of the carrier.

Another distinctly different approach to the problem of navigating to a specimen feature is to offer the operator the means of actually seeing the specimen. One way of doing this is to provide a "viewport" which can be opened to peer into the vacuum chamber through a transparent window of some sort. Practical considerations of geometry and illumination limit the size and effectiveness of such provisions. Further, there are additional engineering considerations which make such viewports more difficult to accomplish than might first be thought—such as the need to provide an x-ray opaque viewing port and the need for an interlock mechanism to disable the light-sensitive imaging detectors when the viewport is opened. Consequently, most SEMs do not incorporate a viewport feature.

Another way of accomplishing much the same thing as the viewport is by interfacing a video camera to the vacuum chamber of the SEM. Some commercial SEMs have been produced which incorporate a video camera, together with an interlocked illumination system, mounted on a port such that the camera views the specimen under the beam. The video camera image provides a "live" view of the specimen, but since illumination must be provided to achieve this image, the normal imaging detectors of the SEM must be disabled to protect them from the effects of this illumination. Also, since the polepiece of the SEM's final probe-forming lens must be located directly over the specimen in order to image, this mandates that the camera view the specimen at a rather oblique angle. The polepiece itself is a rather large structure and the specimen must often be located within a few millimeters of it—this together with the fact that the region immediately above the specimen is rather crowded with other devices such as a backscattered electron detector, a secondary electron detector, and an x-ray detector, tends to restrict the field of view and thus compromise the practical utility of this arrangement as a navigation aid.

A variant of the video camera is the "chamber camera" which has become a moderately popular accessory for SEMs. This device is a small infra-red video camera which is equipped with an infra-red illumination source. Because SEM detectors are insensitive to weak IR illumination, this kind of camera can be used while the microscope is imaging. These devices produce monochrome images and, because they also suffer the same limitations of oblique and crowded viewing conditions as the aforementioned video cameras, they aren't particularly useful for locating features. Instead, their principal application is to help the operator manipulate irregular specimens safely. By mounting such a chamber camera roughly horizontal to the bottom of the polepiece, it is easy to see when the specimen is in danger of contacting the polepiece or one of the detectors. Though very useful, these devices do little to aid the practical problem of specimen navigation.

Electron microprobes (which can be considered to be highly specialized members of the SEM family) have long incorporated an optical microscope as part of their essential equipment. In the traditional design, the light path of the optical microscope is coaxial with the electron beam—a feat accomplished by specialized design of the electron optics. A less common variant is to provide a "side entry" microscope which views the specimen by means of a prism or mirror located immediately over the specimen. These devices, while useful for inspecting the feature being analyzed, have an inherently limited field of view (generally less than that of the electron optics in fact) and are thus of no practical value for specimen navigation.

One solution which has been described in the literature is to implement a separate microscope port with its optical axis parallel to, and offset from, the optical axis of the electron optics. This permits the specimen to be moved between the two viewing modalities by means of the stage. This expedient appears to have been implemented as a means of correlating SEM and light-microscope viewing modalities, rather than as a navigation aid, but it would also lend itself to use of a simple video camera which could capture a "macro" image. However, this implementation imposes both expense and complexity on the design of the microscope. Specifically, in order to allow both the SEM and the camera to view the entire specimen, the size of the specimen chamber and range of travel of the stage must be increased above the minimum required to do either separately. As a consequence, this implementation has not become widely used.

It should be noted that the several solutions described above which employ a camera device are relatively expensive to implement. On the one hand, this is due to the necessity of accommodating the camera to the SEM's vacuum system. Namely, either a vacuum-compatible viewing port must be implemented for the camera, or the camera must itself be vacuum compatible so that it can be contained in the chamber. Secondly, specialized illumination provisions must be implemented, which again increase the cost. This is in contrast to the present invention where there is no requirement for modifications to the specimen chamber, the use of a specialized or modified camera, or a specialized illumination provision.

Within the semiconductor industry, a concept superficially similar to some aspects of the present invention is employed for navigating semiconductor devices. This concept is to employ the design coordinates of a particular semiconductor feature to drive the SEM stage (or other inspection device) to the specified coordinates of the physical device for inspection. This is commonly implemented by means of a graphical user interface which may superficially resemble the kind of graphical user interface described in this invention. The distinction to be made is that the graphical user interface of the present invention is based upon an actual image of the physical device being examined, rather than a "virtual" image created by knowledge of the design parameters of the device, such as is the case for the common semiconductor "navigation" tool.

The invention which is the subject of this disclosure will be shown to be fundamentally different from all of the above implementations in respect to its method of implementation. It will also be demonstrated that an important part of the novelty of this invention is that it provides a very high degree of utility in addressing the fundamental SEM navigation problem with a notably simple and inexpensive apparatus.

SUMMARY OF THE INVENTION

The present invention is an instrument system, such as an electron microscopy system, and a method of control thereof. The method includes acquiring an optical image of an object, with the optical image of the object defining a first coordinate system. The object is positioned in a second, physical coordinate system. In response to selecting a point in the first coordinate system of the optical image, the object is positioned whereupon the point on the object corresponding to the selected point in the optical image is located at a predetermined point in the second coordinate system. Alternatively, in response to repositioning the object, an indicia superimposed on the optical image moves to a point thereon corresponding to a point on the object that is located at the predetermined point in the second coordinate system.

A digital camera can be utilized for acquiring the optical image. The predetermined point in the second coordinate system can be the center of a scan of an electron beam produced by an electron optical column in a manner known in the art. Alternatively, the predetermined point can be one where the tip of another type of probe, such as the physical probe of a micro-indentor or an atomic-force microscope, contacts the surface of the object.

The optical image can be displayed on a monitor. The optical image can be displayed on the monitor with an indicia at the point corresponding to the point in the second coordinate system.

DETAILED DESCRIPTION OF THE INVENTION

Figure 1:
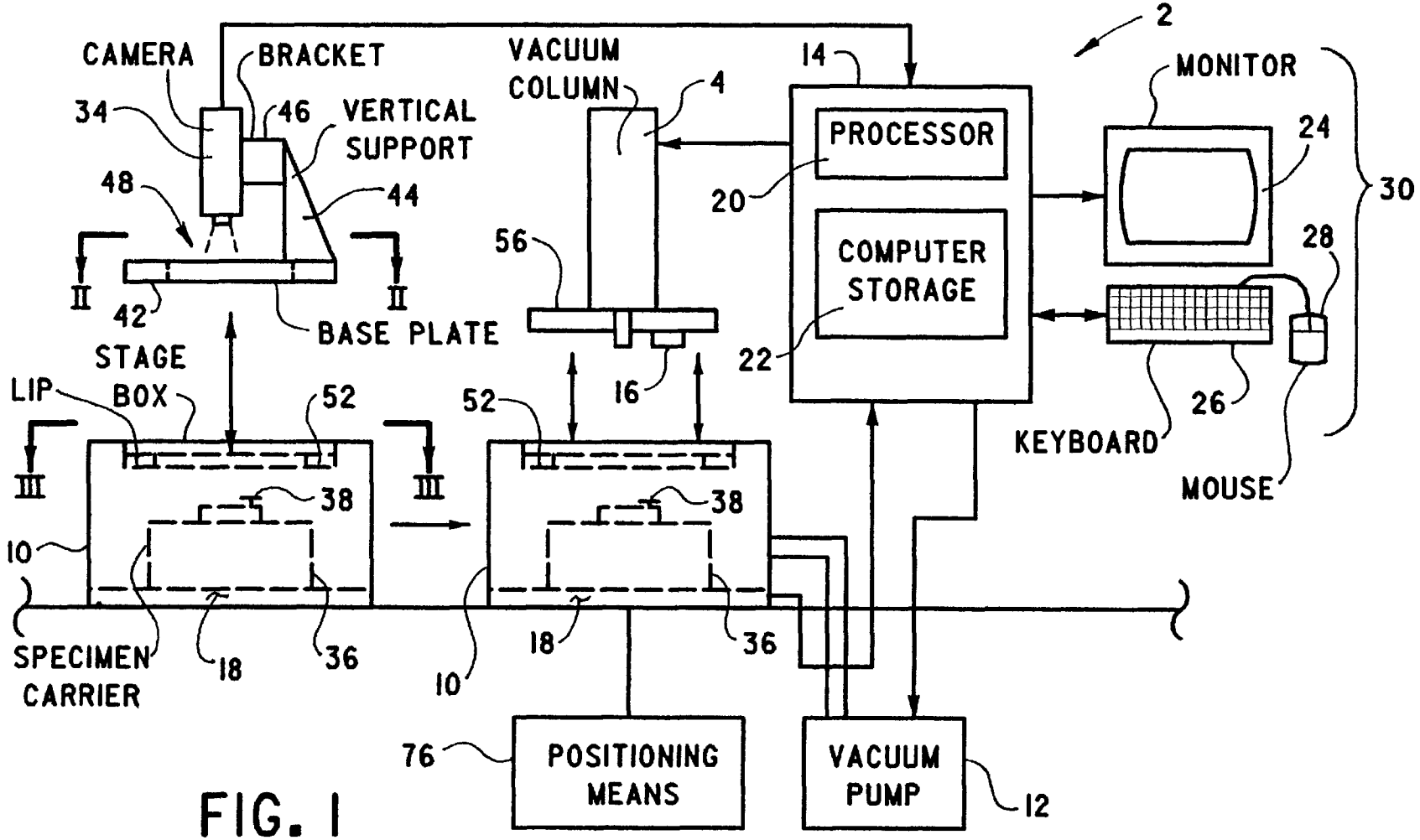
FIG. 1 is a diagrammatic view of an exemplary electron microscopy in accordance with the present invention.

The present invention includes a hardware component and a software component which may be implemented independently, but are most profitably used in conjunction.

The hardware component incorporates an optical image acquisition device (such as an optical digital imaging camera or the like) which is configured to be removably mounted in a predictable position relative to the specimen of a scanning electron microscope (SEM) when the SEM's specimen stage is open or the specimen is removed from the specimen stage. The salient features of this hardware component are as follows:

The image acquisition device may be any of a variety of cameras or image capture devices which are capable of capturing an electronic, optical image which can be accessed and manipulated by electronic means—in particular, a digital, optical image which can be accessed and manipulated by a digital computer. The image acquisition device may be equipped with optics which provide magnification of any desired and appropriate degree, depending upon the other aspects and objectives of the implementation.

The image acquisition device is utilized with mechanical positioning and aligning means as necessary so that it can be mounted in a predictable spatial geometry relative to the specimen when the SEM's stage box is open or when the specimen is removed from the stage.

The image acquisition device and the mounting hardware can be easily demounted or decoupled from the specimen stage or specimen when the specimen is positioned for viewing by the SEM. The nature of the mounting hardware must be such that the image acquisition device can be conveniently coupled and decoupled by an operator without loss of predictable positioning.

Lastly, as an alternative to mounting the image acquisition device in a known geometrical relationship to the specimen stage, the specimen may be first mounted in a fixed position relative to the image acquisition device for purpose of obtaining an optical image, and the specimen then transferred to the specimen stage where it is mounted in a reproducible manner. The net effect of either implementation is that an optical image may be acquired whose spatial relationship to the physical specimen is predictable.

The software component of the invention includes software to accept one or more digital, optical images acquired in known or computable relationship to the physical specimen and to present such optical image or images as a graphical interface by which the SEM operator may cause a particular physical feature of the specimen to be positioned for SEM viewing by "clicking" or otherwise electronically "pointing" to the corresponding feature displayed on the graphical interface. Salient features of the software component are as follows:

One or more previously collected optical images of the specimen's surface, obtained from a digital camera or similar optical image acquisition device, are employed as a graphical aid for navigating the specimen.

The implementation is based on an actual optical image of the physical specimen rather than, for example, mathematical constructs, icons, or "models" of the physical specimen. The optical image may be suitably enhanced by electronic or mathematical means (e.g., contrast adjustment, scaling, cropping, edge sharpening, etc.) without altering the essential nature of the invention.

The software component permits the operator to navigate the specimen stage over large areas of the specimen via reference to the optical image contained in a graphical interface. This optical image may have been captured as a single image or built up from multiple images as a "mosaic" or the like. When built up from multiple images, the optical image need not necessarily be "complete", but may incorporate gaps or "unimaged" areas of the specimen.

Lastly, the software component will typically incorporate calibration features which permit the coordinates of the physical specimen to be accurately referenced to the coordinates of the optical image. Such calibration may be done infrequently or routinely and might incorporate the use of special "calibration specimens". The calibration might also be accomplished by means of known fiducial reference points incorporated in the specimen itself, or the specimen holder into which it is mounted.

The hardware and software components of the invention are normally used in conjunction to create a complete system of the type to be described hereinafter. However, the salient features of either component of the invention do not rely specifically upon the precise implementation of the other. Thus, for example, the hardware component of the invention can be implemented without the software component. Similarly, the software component can be implemented without the hardware component. Specifically, the requirement for the hardware component to provide a predictable spatial orientation to the specimen can be relaxed if the software component is implemented so as to make use of fiducial marks or features of the specimen in order to establish the required geometrical relationships.

The present invention will now be described with reference to the accompanying figures where like reference numbers correspond to like elements.

With reference to FIG. 1, an instrument system, such as electron microscopy system 2, includes an electron optical column 4 that can be hermetically coupled to a specimen stage or stage box 10. Stage box 10 can be coupled in fluid communication with a vacuum pump 12 which, under the control of a computer 14, can draw a suitable vacuum on the interior of stage box 10 when it is coupled in operative relation to a electron optical column 4 via an interface plate 56.

A detector 16 is coupled to interface plate 56 in a manner whereupon detector 16 is positioned inside stage box 10 when it is coupled to interface plate 56. Detector 16 has its output connected to computer 14. Computer 14 is also connected to stage drivers 18 which, in the illustrated embodiment, are positioned inside stage box 10, but which may be positioned outside stage box 10. Stage drivers 18 are positioned at known relative locations with respect to stage box 10. A specimen carrier 36 is positioned inside stage box 10 and is coupled to stage drivers 18. Stage drivers 18 include one or more suitable drive means (not shown), such as a motor. Each drive means includes a suitable position determining means (not shown), such as an encoder, a resolver, a step wise driver and the like. The position determining means outputs position coordinates from which computer 14 can determine the position of stage drivers 18 and, hence, specimen carrier 36 inside stage box 10. Stage drivers 18 and the position determining means can be utilized by computer 14 to effect fine positioning of specimen carrier 36 inside stage box 10. This fine positioning can include moving specimen carrier 36 in one or more of an x, y or z direction, rotating specimen carrier 36 about a vertical axis, or tilting specimen carrier 36 around a horizontal axis.

Computer 14 includes a processor 20 and a computer storage 22. Computer storage 22 includes certain elements known in the art such as RAM, ROM, magnetic or optical storage, and the like which are utilized by processor 20 for permanent or temporary storage of the software component of the present invention (hereinafter "control program") and/or operating parameters of the control program which are utilized to control the operation of electron optical column 4, vacuum pump 12, stage drivers 18 and to interface computer 14 with a man-machine interface 30 that includes, in one exemplary, non-limiting embodiment, a keyboard 26, a mouse 28 and a display monitor 24. Under the control of the operation program, processor 20 also receives data from detector 16 and a camera 34.

Figure 2:
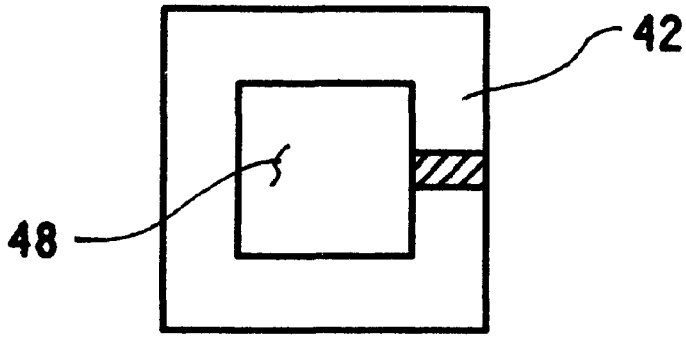
FIG. 2 is a view taken along lines II—II in FIG. 1.
Figure 3:
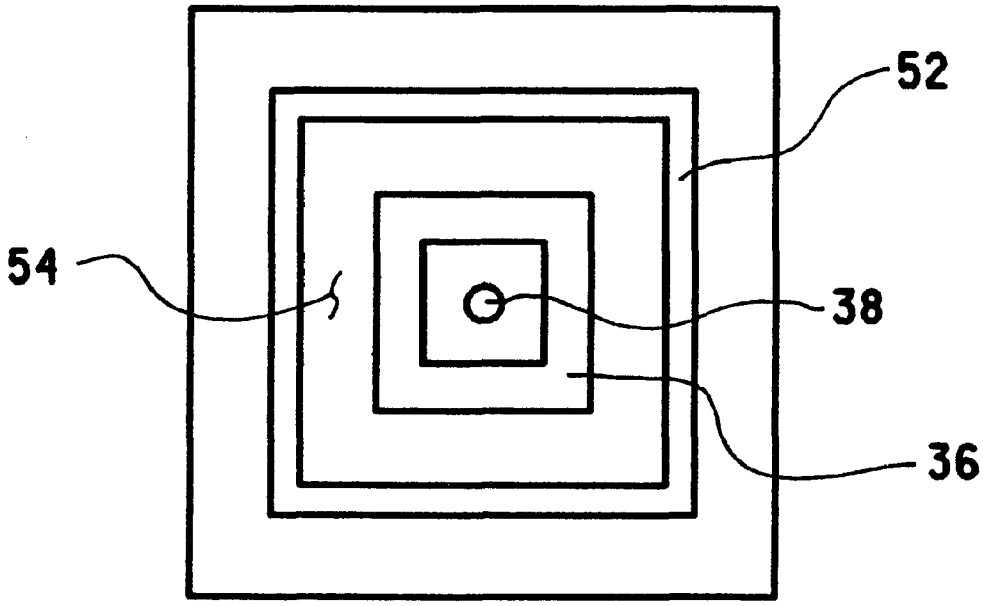
FIG. 3 is a view taken along lines III—III in FIG. 1.

Specimen carrier 36 is configured to support a specimen 38 in stage box 10. With reference to FIGS. 2 and 3 and with continuing reference to FIG. 1, a camera 34 is coupled to a base plate 42 by a vertical support 44 and a bracket 46. As shown best in FIG. 2, base plate 42 includes an aperture 48 therethrough. Vertical support 44 and bracket 46 are configured to support camera 34 so that an input end of input camera 34 can view through aperture 48.

As shown in FIG. 3, stage box 10 includes a recessed lip 52 surrounding an aperture 54 formed in the top of stage box 10. Lip 52 is configured to support base plate 42 around the periphery thereof. With base plate 42 received on lip 52, vertical support 44 and bracket 46 support camera 34 so that the input end of camera 34 can view specimen 38 through apertures 48 and 54.

In operation, specimen or object 38 is positioned on specimen carrier 36 which is positioned inside stage box 10. Thereafter, base plate 42 having camera 34 coupled thereto by vertical support 44 and bracket 46 is positioned on lip 52 with specimen 38 received within the field of view of camera 34.

Under the control of the control program, camera 34 acquires an image of specimen 38 and any other features of specimen carrier 36 in the field-of-view of camera 34. Camera 34 is a digital camera which acquires a digitized optical image of specimen 38. This optical image defines a first coordinate system in which the optical rendering of specimen 38 and/or specimen carrier 36 is received. Under the control of the control program, computer 14 causes camera 34 to transfer the optical image to computer 14 for storage in an appropriate storage media of computer storage 22.

After the optical image is stored in computer storage 22, base plate 42 along with vertical support 44, bracket 46 and camera 34 are removed from lip 52. Thereafter, interface plate 56 is coupled in a fluid tight manner to lip 52 of stage box 10 and vacuum pump 12 is coupled in fluid communication with stage box 10. The coupling of interface plate 56 to lip 52 of stage box 10 positions specimen 38 in a second, physical coordinate system with respect to base plate 56. The foregoing instrument system is for the purpose of describing the present invention and is not to be construed as limiting the present invention since other instrument systems having other features not specifically described herein are also contemplated.

Figure 4:
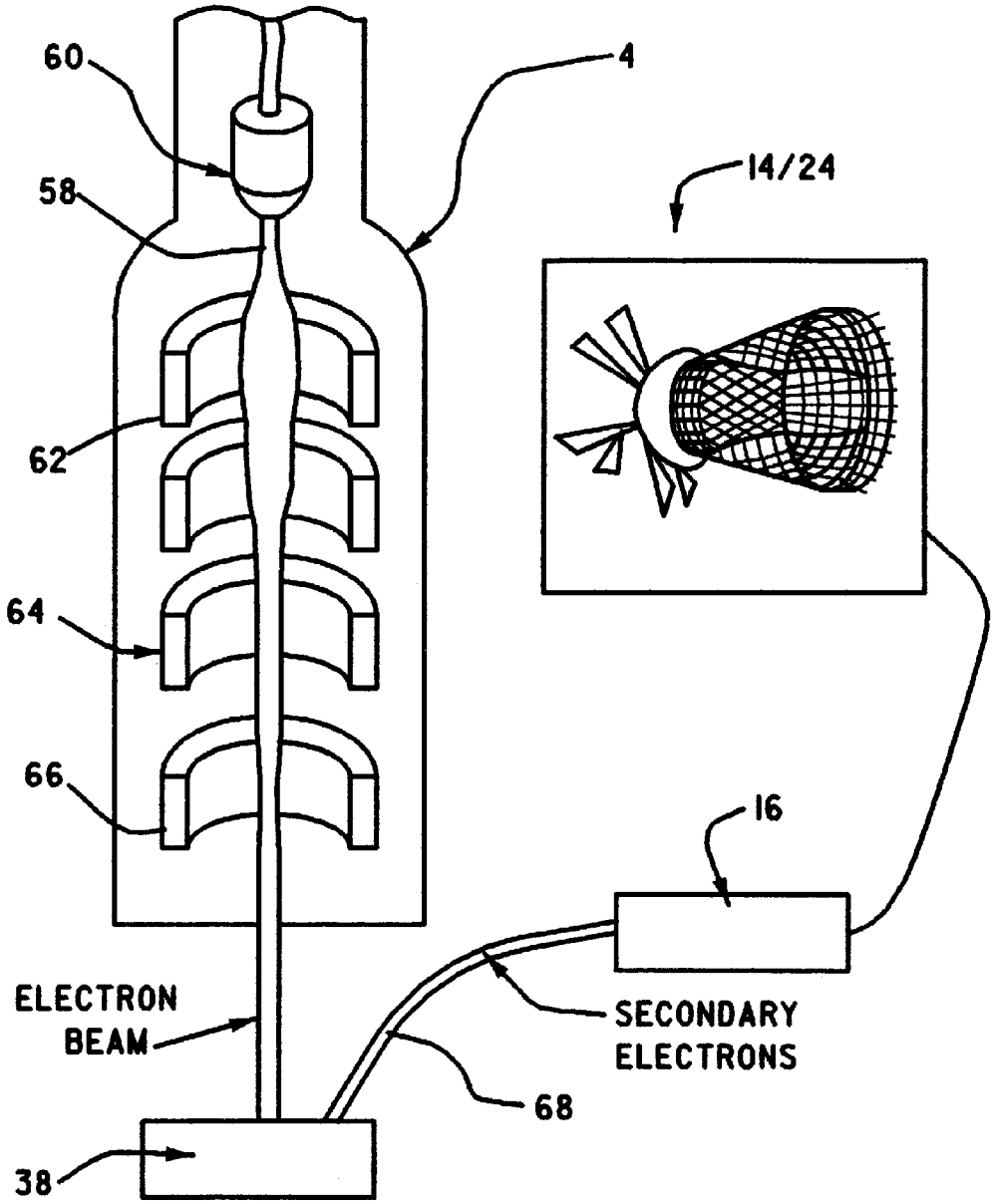
FIG. 4 is an isolated diagrammatic view of the electron optical column, target, detector, computer and monitor shown in FIG. 1.

With reference to FIG. 4 and with continuing reference to FIG. 1, under the control of the control program, computer 14 causes vacuum pump 12 to draw a vacuum on stage box 10 and causes electron optical column 4 to generate and steer an electron beam 58 to a predetermined location within stage box 10 where specimen 38 is located. Electron optical column 4 includes an electron gun 60 which, under the control of computer 14 operating in accordance with the control program, causes an electron beam 58 to be directed toward specimen 38. Electron beam 58 produced by electron gun 60 passes through condensing lenses 62, scan coils 64 and objective lens 66 before striking specimen 38. Operating under the control of the control program, computer 14 causes electron beam 58 to scan or raster an area of specimen 38 and/or specimen carrier 36 in a predictable manner. In response to the scanning of electron beam 58, electrons and/or other signals 68 are emitted for each point in the scan of electron beam 58. Detector 16 is positioned to detect the discharge of the electrons and/or signals 68 and to convert the detected discharge at each point in the scan of electron beam 58 into a electrical signal indicative thereof. Under the control of computer 14 operating in accordance with the control program, the signals output by detector 16 for each point in the scan of electron beam 58 are constructed into a virtual image of specimen 38 and/or specimen carrier 36 which can be displayed on monitor 24.

Figure 5:
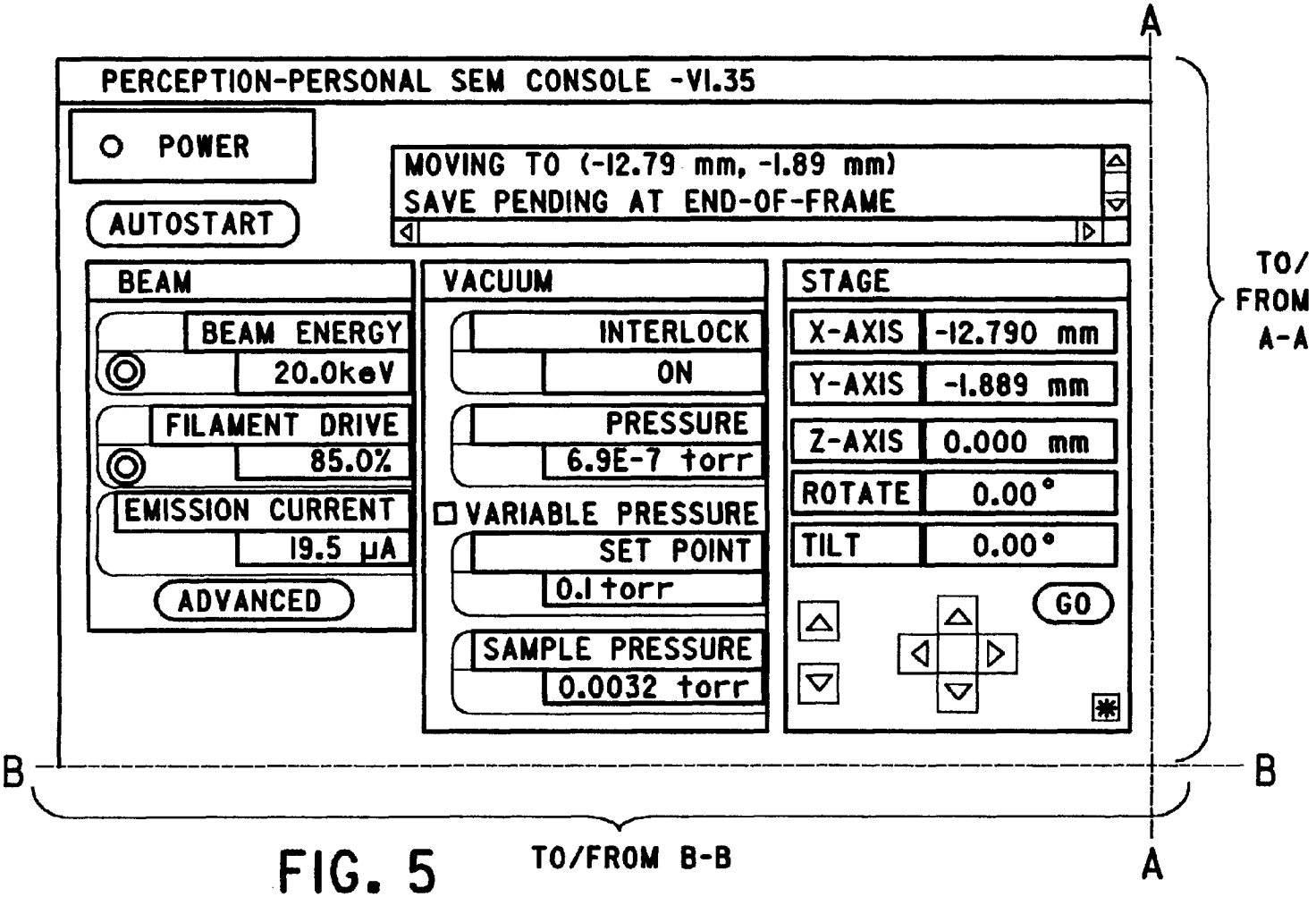
FIG. 5 is a graphical display including an optical image acquired utilizing the camera shown in FIG. 1.
Figure 5A:
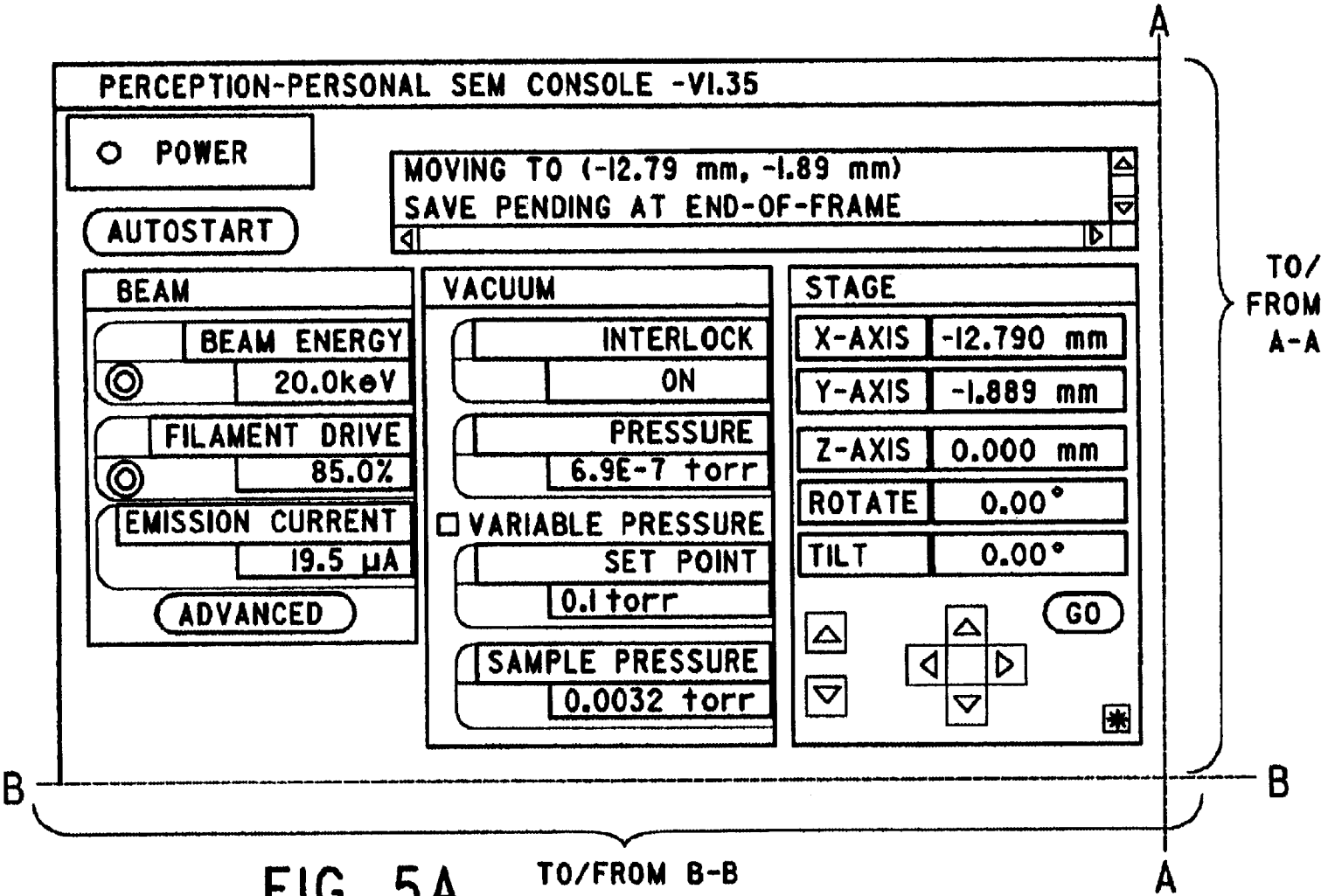
Figure 5B:
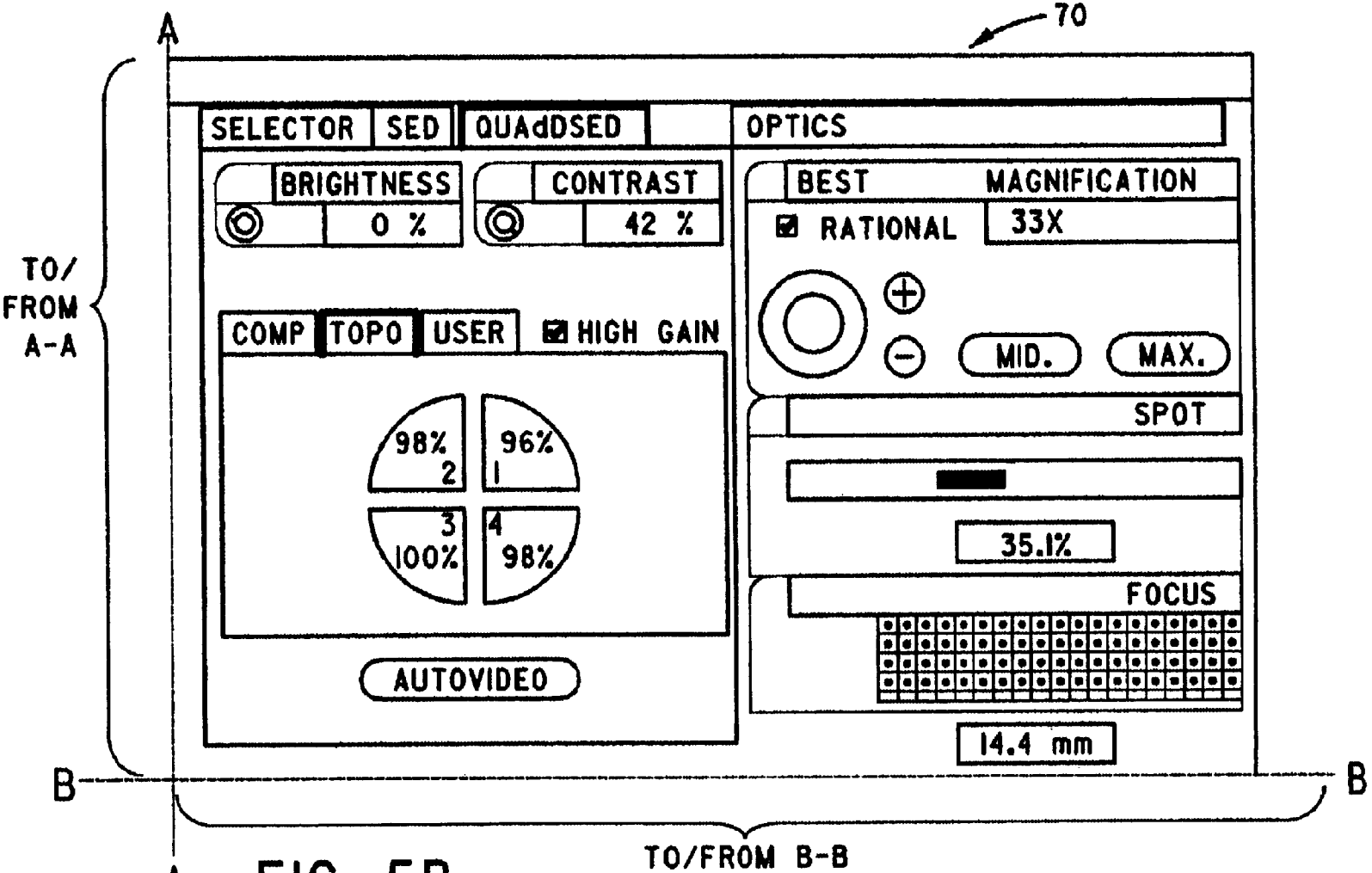
Figure 5C:
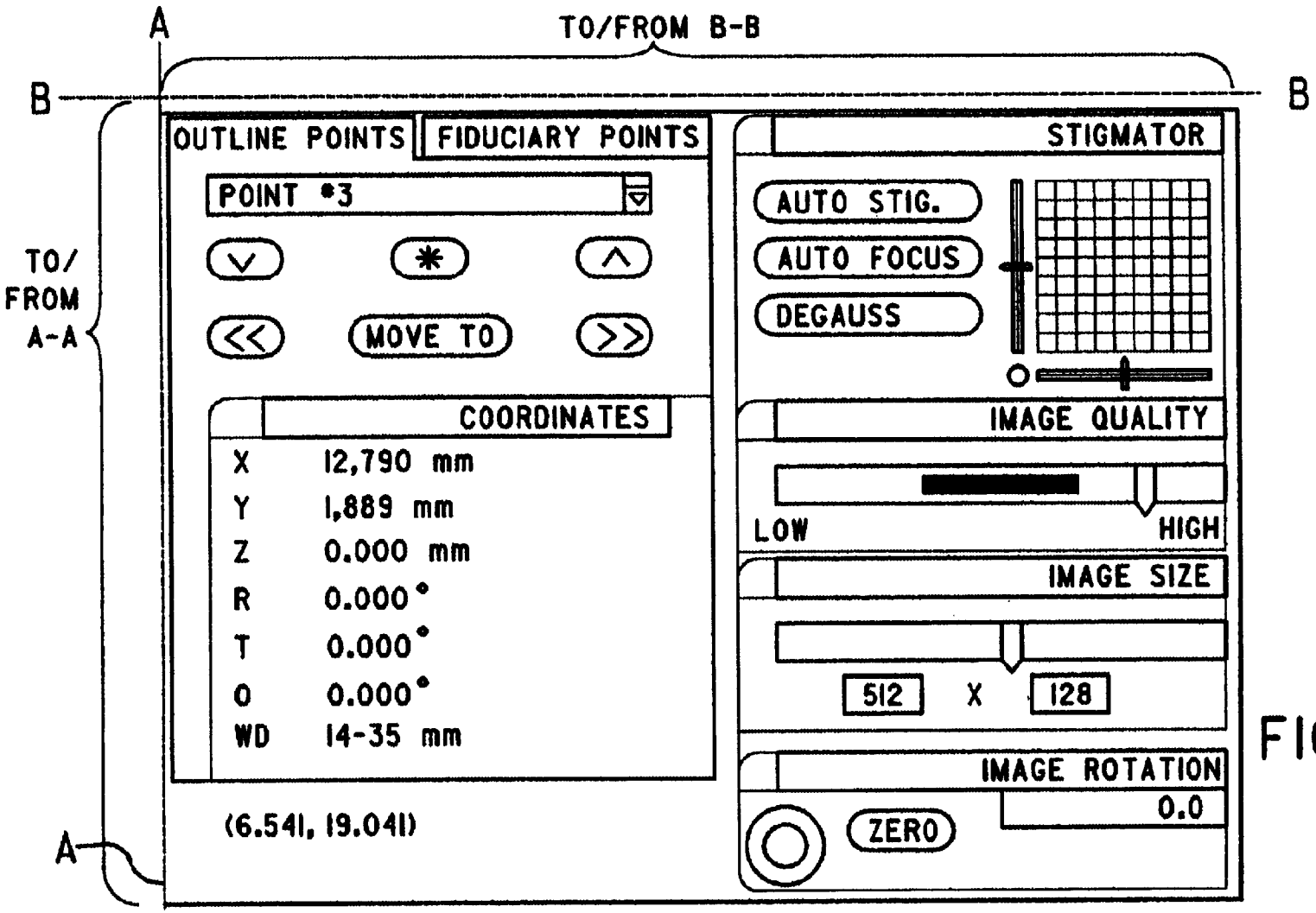
Figure 5D:
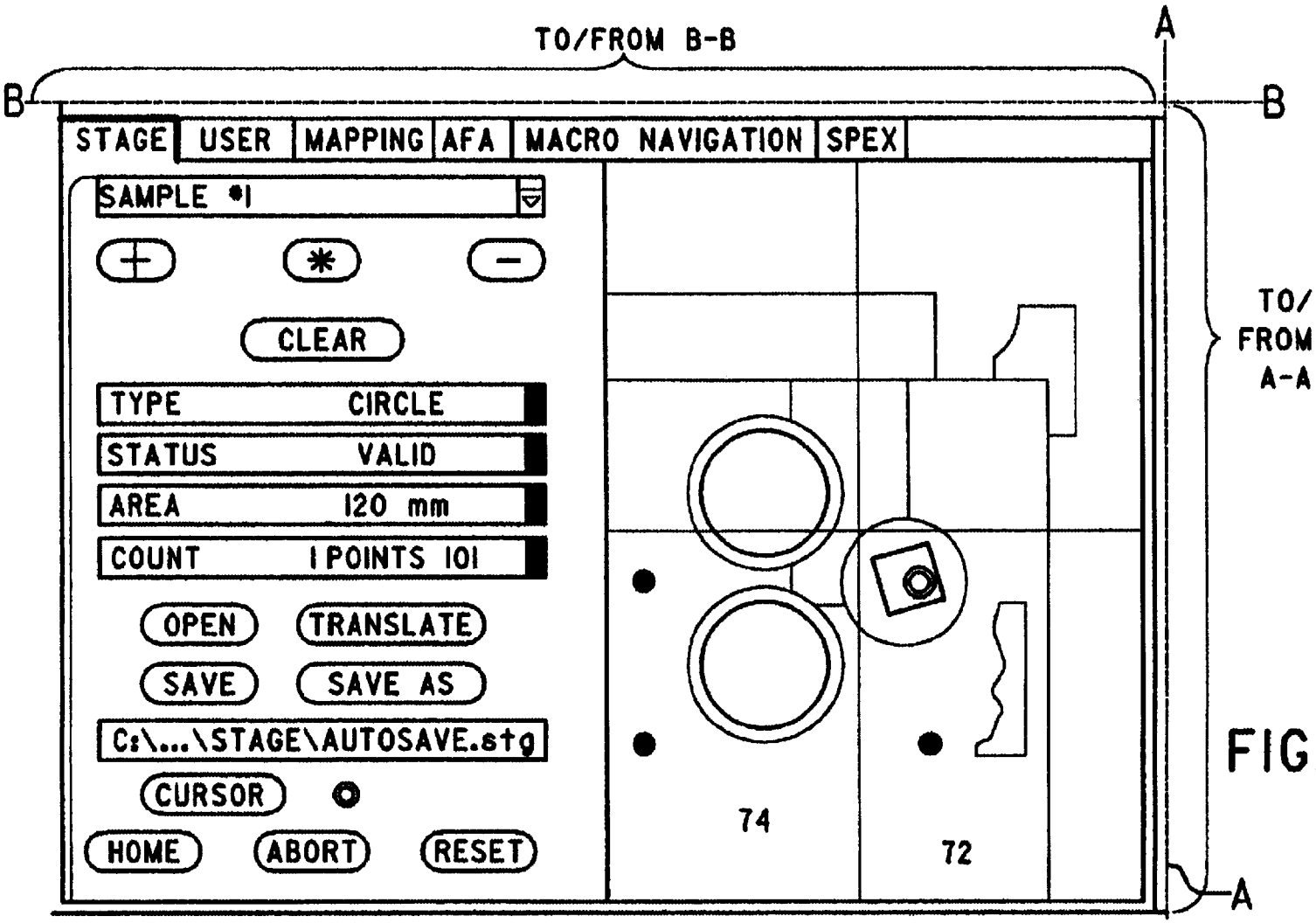

With reference to FIG. 5, and with continuing reference to FIG. 1, the control program can cause computer 14 to display on monitor 24 a graphical console 70. Graphical console 70 can include buttons, dials, sliders and the like which can be selected via mouse 28 utilizing the point and click method, or any other suitable method. In addition, graphical console 70 can include data entry fields which can be selected via mouse 28 utilizing the point and click method, or any other suitable method, and data entered therein via keyboard 26. Graphical console 70 can also include one or more image areas 72 where the optical image acquired by camera 34 and/or the virtual image constructed from the output of detector 16 in response to the scan of electron beam 58 on an area of specimen 38 and/or specimen carrier 36 can be displayed. For simplicity of the following description, graphical console 70 will be described hereinafter as only having one image area 72 in which the optical or virtual image can be alternately displayed under the control of a user of graphical console 70. Image area 72 includes a cross-hair mark 74 or other indicia superimposed on the displayed image. The point in the image where the lines of cross-hair mark 74 cross correspond to a predetermined point in vacuum chamber 6. This predetermined point can be any point where the scan of electron beam 58 strikes specimen 38 or specimen carrier 36. Ideally, however, the intersection of the lines forming cross-hair mark 74 is positioned over a point on the image corresponding to the center of the scan of electron beam 58 on specimen 38 or specimen carrier 36.

Figure 6A:
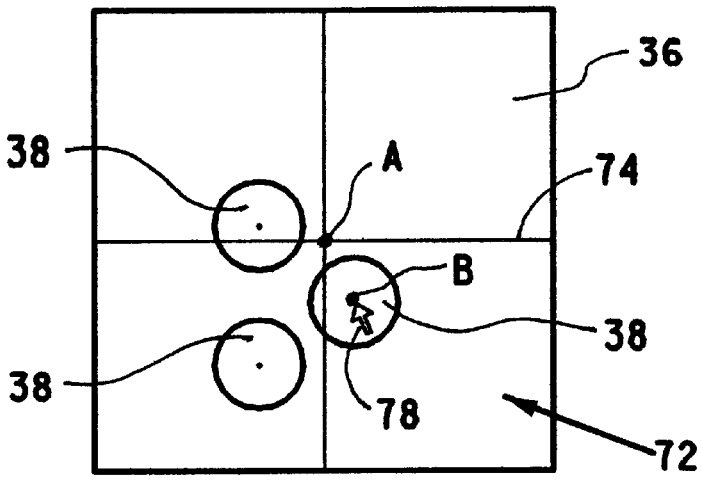
FIG. 6a is an optical image with a first point thereof positioned at a predetermined point represented by the intersection of cross-hairs.

The control program controls computer 14 so that movement of cross-hair mark 74 in image area 72 results in a corresponding movement of specimen carrier 36 via stage drivers 18. More specifically, movement of cross-hair mark 74 on the optical image displayed in image area 72 results in a corresponding movement of specimen carrier 36 relative to electron optical column 4 and detector 16 whereupon the point on the image at the intersection of the lines forming cross-hair mark 74 corresponds to the predetermined point, e.g., the center of the scan of electron beam 58, where electron beam 58 strikes specimen carrier 36 or specimen 38. For example, FIG. 6a shows the optical or virtual image of three specimens 38 on specimen carrier 36. The lines forming cross-hair mark 74 intersect at a point A on this image. This point A can correspond to the current position of the predetermined point, e.g., the center of the scan of electron beam 58, on specimen carrier 36 or specimens 38. However, this is not to be construed as limiting the invention.

Figure 6B:
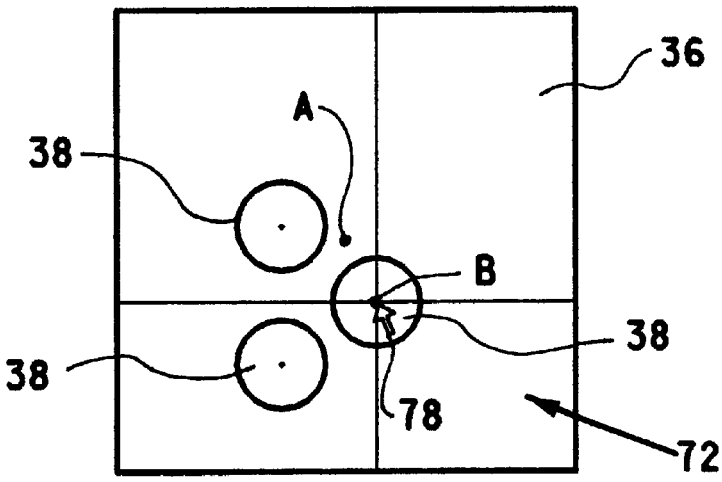
FIG. 6b is the optical image shown in FIG. 6a with the cross-hairs positioned at a second point corresponding to the predetermined point.

Next, suppose that a user utilizes a pointer icon 78 controlled by mouse 28 to point and click a point B on the image. In response to this selection, the control program causes computer 14 to move cross-hair mark 74 on the image whereupon point B is positioned at the intersections of the lines forming cross-hair mark 74 as shown in FIG. 6b. At the same time, computer 14, operating under the control of the control program, causes stage drivers 18 to position specimen carrier 36 so that specimens 38 and specimen carrier 36 are positioned in vacuum chamber 6 with the point thereon corresponding to point B in the image positioned at the predetermined point in the scan of electron beam 58.

More generally, the control program causes computer 14 to define a relationship between the first coordinate system of the image displayed in image area 72 and the second, physical coordinate system where specimen carrier 36 and specimens 38 are positioned. In response to selection of a point in the image and, hence, in the first coordinate system, the control program causes computer 14 to control stage drivers 18 to position specimen carrier 36 so that the corresponding point on specimen carrier 36 or specimens 38 is located at the predetermined point, e.g., the center of the scan of electron beam 58, in the second coordinate system related to the selected point in the first coordinate system.

Alternatively, a user can utilize a positioning means 76 to manually position specimen carrier 36 directly or via stage drivers 18 without having to utilize mouse 28. A suitable positioning means 76 can be one or more micrometers which move specimen carrier 36 directly or a joystick of the type known in the art coupled to drive stage drivers 18. When specimen carrier 36 is moved utilizing positioning means 76, computer 14 monitors the position of specimen carrier 36 inside stage box via the position coordinates output by the position determining means of stage drivers 18.

It is desirable when moving specimen carrier 36 utilizing positioning means 76 that the center of cross-hair mark 74, or other such indicia, be positioned at the point on the optical image corresponding to the predetermined point in the second coordinate system. Accordingly, in response to repositioning the object, the center of cross-hair mark 74 moves to the point on the optical image corresponding to the point on the object that is located at the predetermined point in the second coordinate system.

From the foregoing, it should be appreciated that movement of the center of cross-hair mark 74 relative to the image in image area 72 correlates directly to the movement of specimens 38 and specimen carrier 36 relative to the predetermined point and vice versa. To this end, the control program causes computer 14 to control stage drivers 18 so that specimens 38 and specimen carrier 36 move relative to electron optical column 4 and detector 16 in a manner that corresponds to the movement of cross-hair mark 74 relative to the image in image area 72 and vice versa. Hence, by correlating the first coordinate system of the optical image acquired by camera 34 at a first position and the second, physical coordinate system at a second position where specimens 38 and specimen carrier 38 are located during generation of the virtual image thereof, the position of specimens 38 and specimen carrier 36 relative to electron optical column 4 and detector 16 can be accurately controlled with reference to the optical image and vice versa.

In order to correlate the movement of specimen carrier 36 inside stage box 10 with the movement of the optical image in image area 72, one or more calibrations may be required. These calibrations include: correcting for optical distortions in the optical image, determining a scale factor that can be utilized to establish scale correspondence between the optical image and the motion of specimen carrier 36 and correcting for any offset between the optical image and the virtual image.

Figure 7:
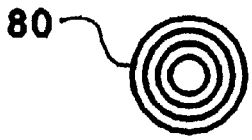
FIG. 7 is a plan view of a target specimen for correcting for barrel distortion in images acquired utilizing the camera of FIG. 1.
Figure 8:
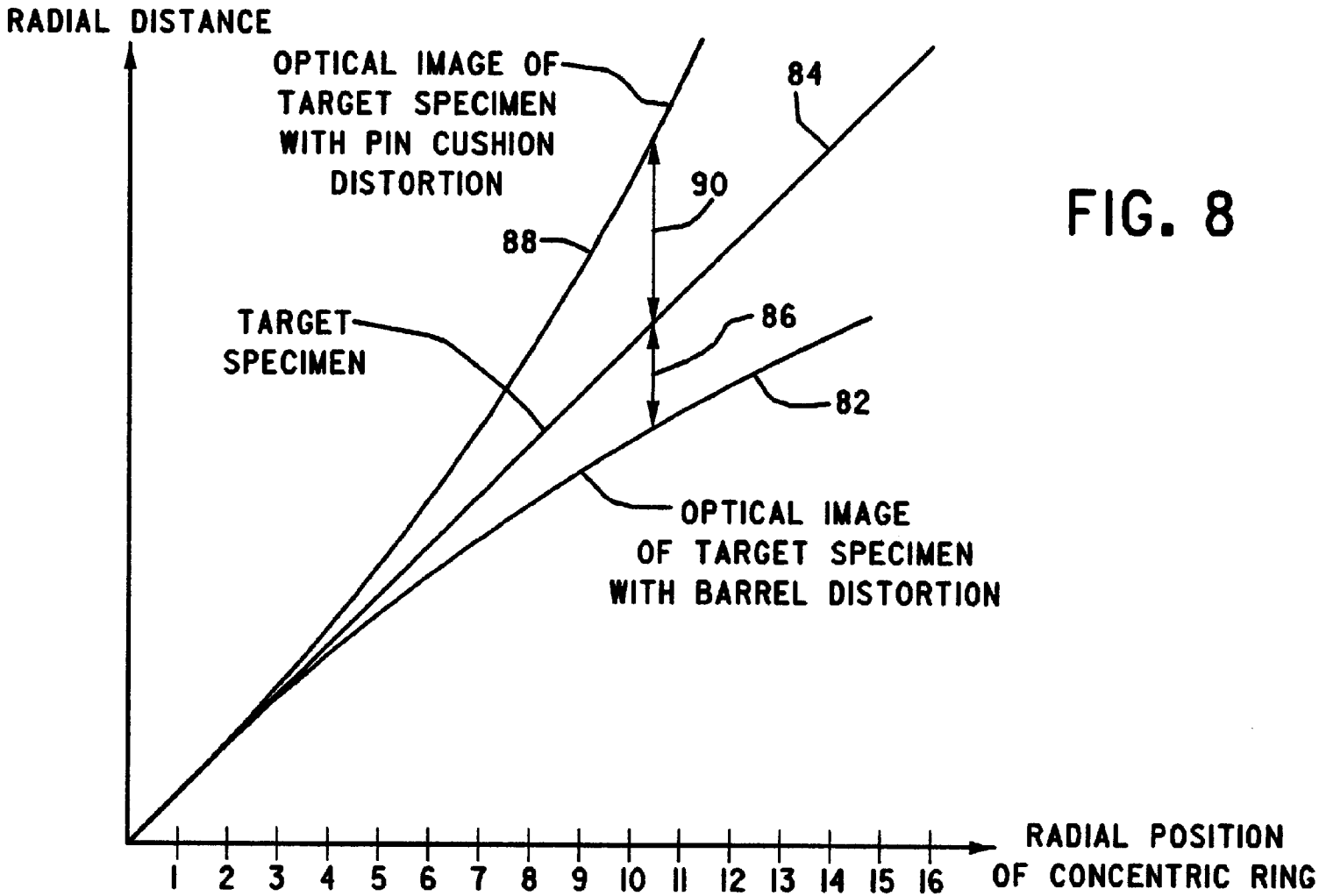
FIG. 8 is a graph of distance versus concentric ring spacing of (1) a target specimen and (2) an optical image of the target specimen illustrating the affects of barrel on caused by the camera shown in FIG. 1.

Optical distortion occurs when camera 34 has significant non-linear distortion of the type known commonly as "barrel distortion" or "pin cushion distortion". Barrel distortion occurs when the spatial scale of the optical image is compressed for points far away from the center thereof, resulting in a concavity of straight line features located near the edge of the field of view of camera 34. Pin cushion distortion occurs when the spatial scale of the optical image is expanded for points far away from the center thereof resulting in a convexity of straight line features located near the edge of the field of view of camera 34. In order to correct for either condition, a target specimen 80, shown in FIG. 7, having a plurality of concentric circles of known spacing, is positioned on specimen carrier 36. An optical image of target specimen 80 is acquired by camera 34 with the center of target specimen 80 located at the center of the acquired optical image. Next, under the control of the control program, computer 14 determines the spacing between each pair of concentric rings in the optical image of target specimen 80. FIG. 8 shows a plot 82 of the observed radial position of concentric rings in the optical image of target specimen 80 as a function of the radial distance from the center of the optical image when barrel distortion is present, a plot 84 of the actual radial position of concentric rings of target specimen 80 as a function of the radial distance from the center of the target specimen 80 and a plot 88 of observed radial position of concentric rings in the optical image of target specimen 80 as a function of the radial distance from the center of the optical image when pin cushion distortion is present. As can be seen, barrel distortion causes the spacing between adjacent concentric rings in the optical image of target specimen 80 to appear smaller than the actual spacing between corresponding concentric rings in the actual target specimen with increasing radial distance from the center of target specimen 80. In contrast, pin cushion distortion causes the spacing between adjacent concentric rings in the optical image of target specimen 80 to appear greater than the actual spacing between corresponding concentric rings in the actual target specimen with increasing radial distance from the center of target specimen 80.

When causing specimen carrier 36 to move in response to causing cross-hair mark 74 to move in image area 72, the control program causes computer 14 to measure a distance between the intersection of the lines of cross-hair mark 74 and the point where the tip of pointer icon 78 is positioned when the user selects this position with mouse 28. Utilizing this radial distance, computer 14 can determine from plots 82 and 84 a radial offset distance 86 or 90 for barrel distortion or pin cushion distortion, respectively, that stage box 10 must be moved by stage drivers 18 in order for specimen 38 or specimen carrier 36 to be positioned at the predetermined point, e.g., the center of the scan of electron beam 58, corresponding to the point on the optical image displayed in image area 72 where the tip of pointer icon 78 is positioned when the user activates mouse 28. More specifically, utilizing well known trigonometric techniques, the control program of computer 14 can determine the additional distance it is necessary to move stage box 10 so that the point on specimen 38 or specimen carrier 36, corresponding to the point in the optical image selected by the user, is positioned at the predetermined point in the scan of electron beam 58.

The data utilized to form plots 82 or 88 need only be acquired once for a given camera 34 and can thereafter be stored for subsequent use.

One method to establish scale correspondence between the optical image and the motion of specimen carrier 36 inside stage box 10 includes positioning camera 34 on stage box 10, in the above described manner, to view specimen 38 and/or specimen carrier 36. Thereafter, a first optical image is acquired. An operator then moves pointer icon 78 to an identifiable feature in the first optical image and selects this feature via mouse 28. In response to selecting this feature in the first optical image, the control program records a first pixel location of the feature in the first optical image and records first position coordinates output by the position determining means. Next, stage drivers 18 displace specimen carrier 36 by a predetermined distance and camera 34 acquires a second optical image. Thereafter, utilizing mouse 28, the operator selects the same feature in the second optical image, which will of course now be located at a different position. In response to selecting the feature in the second optical image, the control program records a second pixel location of the feature in the second optical image and records second position coordinates output by the position determining means. The control program then determines a ratio between the first and second pixel locations and the distance between the first and second position coordinates to obtain the scale factor that can be utilized to establish scale correspondence between the optical image and the motion of specimen carrier 36.

Another method to establish scale correspondence between the optical image and the motion of specimen carrier 36 inside stage box 10 includes acquiring an optical image and a first virtual image of specimen 38 and/or specimen carrier 36. Thereafter, the operator moves pointer icon 78 to a first identifiable feature in the first virtual image and selects this feature via mouse 28. In response to selecting this first feature, the control program records first position coordinates output by the position determining means. Then, the operator selects the first feature in the optical image. In response to selecting the first feature in the optical image, the control program records a first pixel location of the feature in the optical image. Next, stage drivers 18 displace specimen carrier 36 by a predetermined distance and a second virtual image is acquired. Thereafter, the operator moves pointer icon 78 to a second identifiable feature in the second virtual image and selects this feature via mouse 28. In response to selecting this second feature, the control program records second position coordinates output by the position determining means. Then, the operator selects the second feature in the optical image. In response to selecting the second feature in the optical image, the control program records a second pixel location of the feature in the optical image. The control program then determines a ratio between the first and second pixel locations in the optical image and the distance between the first and second coordinates to obtain the scale factor that can be utilized to establish scale correspondence between the optical image and the motion of specimen carrier 36.

Because this ratio will change whenever the distance of the specimen 38 relative to camera 34 changes, the foregoing scale calibration should be repeated whenever the height of the sample or when the size of the optical image of the object acquired by the camera changes significantly.

Once the optical distortion and scale have been properly calibrated, it is still necessary to establish the linear translation or offset between the position of specimen 38 or specimen carrier 36 and a point on the optical image. This is accomplished by simply comparing the virtual image to the optical image and clicking on the same identifiable feature in both images.

Utilizing these simple procedures, or others that can be equivalently devised, it is possible to establish precise spatial correspondence between the optical image and the physical coordinates of specimen 38 or specimen carrier 36 when it is positioned in the scan of electron beam 58. It is then a simple matter to translate locations selected in the optical image to coordinates of stage drivers 18 that will bring the corresponding feature to the predetermined point in the scan of electron beam 58.

The foregoing is a particular implementation of the invention. However, variances of the foregoing implementation are possible within the scope of the present invention. For example, rather than being adapted for placing on top of stage box 10, base plate 42 can be equipped with a fixture (not shown) which holds specimen carrier 36 in a fixed geometry. An equivalent fixture can also be disposed inside stage box 10 to hold specimen carrier 36 therein. In use, specimen carrier 36 is held by the fixture in a position where camera 34 can acquire an optical image of specimen 38. The specimen carrier 36 is then physically transferred to the corresponding fixture inside of stage box 10. Since both fixtures are constructed to position specimen carrier 36 in an equivalent way, it is possible to directly correlate the features of the acquired optical image to the corresponding coordinates of stage drivers 18.

In another variant, correspondence between pixel coordinates of the optical image and coordinates of stage drivers 18 can be accomplished mathematically by establishing the correspondence of two or more suitably chosen features of the optical image with their corresponding coordinates of stage drivers 18. For example, if two fiducial marks are provided on specimen carrier 36, the known spacing between these marks may be used to establish the scale of the optical image. Moreover, the known position of one of these marks may be used to establish the offset for a linear spatial transformation relating the coordinates of the optical image pixels with the coordinates of stage drivers 18. In this way, the requirement for a rigorously predictable mechanical relationship between camera 34 and specimen 38 is eliminated. Instead, the predictable relationship is accomplished by strictly mathematical means by reference to features of known positions visible in the optical image.

The embodiment of the invention described in connection with FIGS. 1-8 was described with an assumption of planar (x, y) positioning. In practice, however, many stage drivers 18 are implemented with additional coordinate axes for Z motion (height), R motion (rotation), and/or T motion (tilt). Incorporation of these additional motion axes in the subject invention can be handled in a straightforward manner by replacing planar transformation equations with more general transformation equations appropriate to the stage geometry.

In the case of a stage with a rotation axis perpendicular to the typical x, y motion axes, the appropriate transformation equations will simply be the familiar planar equations for translation with rotation. Knowledge of the rotation angle will typically be obtained directly from stage drivers 18, but may in some instances need to be calibrated. It may also be necessary to establish the center of rotation by a calibration procedure. The functionality of these transformation equations can also be employed in multiple ways. For example, the control program may be implemented such that selecting a point in the optical image will cause stage drivers 18 to move specimen 38 and specimen carrier 36 to the indicated x, y coordinates to bring the indicated point to the predetermined point in the scan of electron beam 58, and also to cause an electronic scan orientation of computer 14 to be oriented to match the rotation of specimen 38, thus causing the resulting virtual image to be displayed in the same orientation as the optical image.

For stage drivers 18 with motorized (or electronically encoded) Z motion, appropriate transformation equations and corresponding calibration procedures can again be readily constructed. In this case, a change in the height of specimen 38 introduces a uniform change of scale in the amount of planar (x, y) motion required to achieve a given displacement relative to the features of the optical image. Establishing the appropriate change of scale can be accomplished either by knowledge of the stage drivers 18 operation, by a calibration procedure, or a combination of both.

In the case of utilizing specimen 38, the effect of a tilt is to introduce a foreshortening of the apparent motion scale along an axis perpendicular to the tilt axis. For example, for a specimen tilted at a 45 degree angle, the amount of stage displacement along an axis perpendicular to the tilt axis will be $1/\sqrt{2}$ the size of the stage displacement required to produce the same magnitude of displacement in the SEM image for the untilted specimen. This scale transformation might be implemented either by an appropriate directional compression of the optical image, or more simply, by utilizing the coordinates of the untilted optical image to reference the stage drivers 18 coordinates of the comparable features of tilted specimen 38.

The specific transformation equations and calibration procedures required to accommodate a particular implementation of stage drivers 18 will depend on the details of stage drivers 18. For example, implementing tilt axis T such that the x, y axes themselves are tilted relative to a fixed reference plane will result in very different equations from the case in which the tilt T is applied to an axis superimposed on a fixed x, y reference plane. Similarly, if the Z axis is not perpendicular to the x, y axis plane, the coordinate transformation must accommodate an apparent translation in x, y coordinates due to a change in Z position. These variations and the appropriate means of accommodating them are too numerous to detail, but will be obvious to anyone with ordinary skill in the art of positioning systems. The germane point, relevant to the scope of this invention, is that, regardless of the number and type of positioning axes implemented, that appropriate transformation equations and their corresponding calibration procedures are implemented such that the coordinates of a feature identified in the optical image may be employed to position the axes of stage drivers 18 so as to bring the selected physical feature of a substantially planar specimen 38 into a desired position in the scan of electron beam 58.

In the case of a three-dimensional specimen 38 of arbitrary shape, it will be apparent that unless detailed knowledge of the specimen's overall shape is available, it is not possible to establish transformation equations which project the location of a feature on the surface of such an arbitrary three-dimensional specimen onto the coordinates of the two-dimensional optical image plane under arbitrary sample tilt conditions. However, the following situations are anticipated: (a) specimen 38 can be approximated by a planar surface. For example, a loaded printed circuit board can be conveniently navigated by reference to the planar surface of the board itself. The apparent position of an elevated component mounted on the board will suffer a parallax displacement when the board is tilted, but this is easily accommodated by the user; (b) a series of optical images can be employed to provide appropriate views of the specimen. Since any surface can be approximated as a planar surface for a sufficiently small tilt, it would in principle be possible to employ this scheme in any arbitrary situation. However, in practice, its utility would be limited to those situations where the specimen is not highly contoured and/or the anticipated range of tilt angles is small; (c) the overall shape of the specimen is known in advance. For example, it is a simple matter to generate the appropriate transformation equations for points on the surface of a rectangular solid of known dimensions.

All modern electron microscopes are equipped with means for changing the size of the scanning raster (magnification) and its orientation (rotation). Issues of magnification and rotation may simply be ignored if the above invention is applied so as to move the feature selected on the optical image to the center of the virtual image. On the other hand, for purposes of enhancing the functionality of the subject invention, the scan magnification and rotation may be explicitly incorporated in the transformation equations and associated calibration procedures. The modifications to the transformation equations to accomplish this are similar to, but distinct from those employed for stage x, y motion with rotation and may be readily derived by a practitioner with skill in the art.

For the case of a very large specimen, the resolution of the imaging camera may not provide a sufficiently detailed picture to be useful as a navigation aid. In such a case, it is anticipated that multiple images of the specimen surface may be employed, either as individually selectable views, or merged together to form a single large "mosaic" image.

The invention has been described with reference to the preferred embodiments. Obvious modifications and alterations will occur to others upon reading and understanding the preceding detailed description. For example, while described in connection with an electron microscopy system, the present invention can be utilized with any instrument system where movement of an object in one coordinate system is correlated with movement of a marker superimposed on an image of the object defining another coordinate system. Examples of such instrument systems include a micro-indentor and an atomic force microscope. In these systems, a mechanical means, such as a probe, is utilized to contact the surface of the specimen, versus an electron beam contacting the specimen. It is intended that the invention be construed as including all such modifications and alterations insofar as they come within the scope of the appended claims or the equivalents thereof.

The invention is claimed to be:

1. [An instrument system] *A system for navigating an object in an electron microscope without prior manual traversal of the object,* comprising:

a camera for acquiring an optical image of [an] *the* object, the optical image defining a first coordinate system;

means for positioning the object [in], *the positioning means defining* a second coordinate system *relative to an electron beam of the electron microscope, the optical image representing a substantial portion of the second coordinate system*;

means for adjusting the position of the object in the second coordinate system; and a computer operative for storing the optical image, for defining a relationship between the first and second coordinate systems and for at least one of:

(i) causing the adjusting means to move the object *within the second coordinate system* in response to selection of a point in the first coordinate system corresponding to a point on the optical image, so that the point on the object corresponding to the point on the optical image is located at [a point in the second coordinate system related to the selected point in the first coordinate system] *the electron beam of the electron microscope, thereby causing a selected portion of the object to be viewable by the electron microscope*; and (ii) causing an indicia superimposed on the optical image to move to a point in the first coordinate system corresponding to the point in the second coordinate system *that is located at the electron beam of the electron microscope,* in response to moving the object in the second coordinate system.

2. The system as set forth in claim 1, wherein the computer includes a processor and memory means.

3. The system as set forth in claim 1, further including a monitor operatively connected to the computer.

4. The system as set forth in claim 1, further including means for positioning the digital camera and the object relative to each other in a predictable spatial manner during acquisition of the optical image.

5. The system as set forth in claim 1, wherein the computer is further operative for at least one of (i) correcting for optical distortion between the optical image and the object, (ii) correcting for a scale difference between optical image and the object, and (iii) correcting for an offset difference between a point in the optical image and a corresponding point on the object.

6. The system as set forth in claim 5, wherein, to correct for optical distortion, the computer is operative for acquiring an image of a target object having a plurality of concentric circles of known spacing, for determining a distance between each pair of concentric circles in the optical image, for determining a relationship between the distance between each pair of concentric circles in the optical image and the actual distance between each pair of concentric circles of the target object and for causing the adjusting means to position the object as a function of the determined relationship.

7. The system as set forth in claim 5, wherein, to correct for the scale difference, the computer is operative for acquiring a first optical image of an object, for recording a first location in the first optical image where a reference point is located, for recording a first position of the adjusting means related to the first location in the first optical image, for causing the adjusting means to displace the object, for acquiring a second optical image of the object, for recording a second location in the second optical image where the reference point is located, for recording a second position of the adjusting means related to the second location in the second optical image, for determining a ratio between the first and second locations and the first and second positions and for causing the adjusting means to position the object as a function of the thus determined ratio.

8. The system as set forth in claim 5, wherein, to correct for the scale difference, the computer is operative for acquiring an optical image and a first virtual test image of an object, for recording a first position of the adjusting means related to a location of a first feature in the first virtual test image, for recording a first location in the optical image where the first feature is located, for causing the adjusting means to displace the object, for acquiring a second virtual test image of the object, for recording a second position of the adjusting means related to a location of a second feature in the second virtual test image, for recording a second location in the optical image where the second feature is located, for determining a ratio between the first and second locations and the first and second positions and for causing the adjusting means to position the object as a function of the thus determined ratio.

9. The system as set forth in claim 5, further including a detector for detecting the response of the object to an electron beam and for supplying an indication of the detected response to the computer, wherein, to correct for the offset difference, the computer is operative for constructing a virtual image of the object from the indication of the detected response, for displaying the virtual image, for receiving the selection of a reference point in the virtual image, for determining a position in the virtual image corresponding to the selected reference point therein, for displaying the optical image, for receiving the selection of a corresponding reference point in the optical image, for determining a position in the optical image corresponding to the selected reference point therein, for determining a difference between the positions in the virtual and optical images and for causing the adjusting means to position the object as a function of the thus determined difference.

10. A computer-assisted method of [controlling an instrument system] *navigating an object in an electron microscope without prior manual traversal of the object* comprising the steps of:

acquiring an optical image of [an] *the* object, the optical image defining a first coordinate system;

positioning the object in a second coordinate system [having a predetermined relation to the first coordinate system] *relative to an electron beam of the electron micro-*

*scope, the optical image representing a substantial portion of the second coordinate system*; and at least one of:

in response to selecting a point in the first coordinate system *of the optical image*, repositioning the object *within the second coordinate system,* whereupon a point on the object corresponding to the selected point *in the optical image* is located at [a point in the second coordinate system related to the selected point in the first coordinate system] *the electron beam of the electron microscope, thereby causing a selected portion of the object to be viewable by the electron microscope*; and in response to repositioning the object *within the second coordinate system*, moving an indicia superimposed on the optical image to a point [thereon] *on the optical image* corresponding to a point on the object that is located at the [predetermined point in the second coordinate system] *electron beam of the electron microscope*.

11. The method as set forth in claim 10, further comprising at least one of the steps of:

correcting for optical distortion between points in the optical image and corresponding points of the object;

correcting for a scale difference in the distance between two points in the optical image and two corresponding points of the object; and correcting for an offset difference between a point in the optical image and a corresponding point of the object.

12. The method as set forth in claim 11, wherein the step of correcting for optical distortion includes the steps of:

acquiring an image of a target object having a plurality of concentric circles of known spacing;

determining a distance between each pair of concentric circles in the optical image;

determining a relationship between the distance between each pair of concentric circles in the optical image and the actual distance between each pair of concentric circles of the target object; and positioning the object as a function of the thus determined relationship.

13. The method as set forth in claim 11, wherein the step of correcting for the scale difference includes the steps of:

selecting a first reference point in a first optical image;

recording a first location in the first optical image where the first reference point is located;

recording a first position of the adjusting means related to the first location of the first reference point;

adjusting the position of the object;

selecting a second reference point in a second optical image;

recording a second location in the second optical image where the second reference point is located;

recording a second position of the adjusting means related to the second location of the second reference point;

determining a ratio between the first and second positions and the first and second locations; and positioning the object as a function of the thus determined ratio.

14. The method as set forth in claim 11, wherein the step of correcting for the scale difference includes the steps of:

acquiring an optical image and a first virtual image of an object;

recording a first position of the adjusting means related to a location of a first feature in the first virtual image;

recording a first location in the optical image where the first feature is located;

moving the object;

acquiring a second virtual image of the object;

recording a second position of the adjusting means related to a location of a second feature in the second virtual image;

recording a second location in the optical image where the second feature is located;

determining a ratio between the first and second locations and the first and second positions; and causing the adjusting means to position the object as a function of the thus determined ratio.

15. The method as set forth in claim 11, wherein the step of correcting for the offset difference includes the steps of:

detecting the response of the object to an electron beam;

constructing a scanning electron microscope (virtual) image of the object from the detected response;

selecting a reference point in the virtual image;

determining a position in the virtual image corresponding to the selected reference point therein;

selecting a reference point in the optical image corresponding to the reference point selected in the virtual image;

determining a position in the optical image corresponding to the selected reference point therein;

determining a difference between the positions in the virtual and optical images; and positioning the object as a function of the thus determined difference.

16. [An instrument apparatus] *A system for navigating an object in an electron microscope without prior manual traversal of the object* comprising:

means for acquiring an optical image of [an] *the* object, the optical image defining a first coordinate system;

means for positioning the object [in], *the positioning means defining* a second coordinate system [related to the first coordinate system] *relative to an electron beam of the electron microscope, the optical image representing a substantial portion of the second coordinate system*; and at least one of:

(i) means responsive to the selection of a point in the *first coordinate system of the* optical image for causing the positioning means to position the object *within the second coordinate system,* whereupon a point on the object corresponding to the selected point in the optical image is located at [a predetermined point in the second coordinate system] *the electron beam of the electron microscope, thereby causing a selected portion of the object to be viewable by the electron microscope*; and (ii) means responsive to the positioning means moving the object in the second coordinate system whereupon an indicia on the optical image moves to a point thereon corresponding to the point on the object that is located at the [predetermined point in the second coordinate system] *electron beam of the electron microscope*.

17. The apparatus as set forth in claim 16, further including means for constructing a virtual image of the object.

18. The apparatus as set forth in claim 17, wherein the constructing means includes:

means responsive to interaction between the object and an electron beam at the second location for outputting an indication thereof; and means responsive to the output indication for constructing the virtual image of the object.

*19. The system of claim 1, wherein the optical image corresponds to at least 10% of the second coordinate system by area.*

*20. The system of claim 1, wherein the optical image corresponds to at least 25% of the second coordinate system by area.*

*21. The system of claim 1, wherein the optical image comprises multiple images arranged in a mosaic.*

*22. The system of claim 1, wherein the electron microscope is a scanning electron microscope.*

*23. The method of claim 10, wherein the optical image corresponds to at least 10% of the second coordinate system by area.*

*24. The method of claim 10, wherein the optical image corresponds to at least 25% of the second coordinate system by area.*

*25. The method of claim 10, wherein the electron microscope is a scanning electron microscope.*

*26. The method of claim 10, wherein the optical image comprises multiple images arranged in a mosaic.*

*27. The system of claim 16, wherein the optical image comprises multiple images arranged in a mosaic.*

*28. The system of claim 16, wherein the optical image corresponds to at least 10% of the second coordinate system by area.*

*29. The system of claim 16, wherein the optical image corresponds to at least 25% of the second coordinate system by area.*

*30. The system of claim 16, wherein the electron microscope is a scanning electron microscope.*

* * * * *